US012778705B2

(12) United States Patent
Burgess et al.

(10) Patent No.: US 12,778,705 B2
(45) Date of Patent: Nov. 3, 2026

(54) SHARPS CONTAINER

(71) Applicant: Medline Industries, LP, Northfield, IL (US)

(72) Inventors: James Burgess, Lake Bluff, IL (US); Scott Bedoe, McHenry, IL (US); Hongmeng Tian, Shenzhen (CN)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 18/828,777

(22) Filed: Sep. 9, 2024

(65) Prior Publication Data

US 2024/0423745 A1 Dec. 26, 2024

Related U.S. Application Data

(63) Continuation of application No. 18/099,163, filed on Jan. 19, 2023, now Pat. No. 12,082,951, which is a continuation of application No. 16/845,842, filed on Apr. 10, 2020, now Pat. No. 11,559,369, which is a continuation of application No. 16/436,920, filed on Jun. 11, 2019, now Pat. No. 10,617,485, which is a continuation of application No. 14/921,586, filed on Oct. 23, 2015, now Pat. No. 10,321,968.

(51) Int. Cl.
*A61B 50/36* (2016.01)
*A61B 50/00* (2016.01)
*A61B 50/37* (2016.01)

(52) U.S. Cl.
CPC ............ *A61B 50/36* (2016.02); *A61B 50/362* (2016.02); *A61B 50/37* (2016.02); *A61B 2050/005* (2016.02); *A61B 2050/375* (2016.02)

(58) Field of Classification Search
CPC ....... A61B 50/37; A61B 50/36; A61B 50/362; A61B 2050/0083; A61B 50/00; B65F 1/10
See application file for complete search history.

(56) References Cited

U.S. PATENT DOCUMENTS 2,351,597 A 6/1944 Burlin
2,634,933 A 4/1953 Grimsley
(Continued)

FOREIGN PATENT DOCUMENTS

AU 686587 B2 2/1998
DE 890623 9/1953
(Continued)

*Primary Examiner* — Jeffrey R Allen
(74) *Attorney, Agent, or Firm* — SandBright Intellectual Property; Robert D. Spendlove

(57) ABSTRACT

A container for disposal of medical waste is provided that comprises a receptacle with an open top. A lid is attached to the receptacle to cover the open top of the receptacle. The lid has an elongated opening sized to permit the introduction of medical waste into the receptacle. A closure flap is connected to the lid to selectively close the lid opening. The closure flap is movable between an open position, a closed position, and a locked position. The closure flap is attached to the lid by axial hubs that extend from each side of the closure flap through openings in the side walls of the lid. Covers attached to the outside of the side wall of the lid and engaged with the closure flap axial hub. The container may also include a locking external cabinet that encloses the receptacle and can be mounted to a wall.

20 Claims, 11 Drawing Sheets

(56) References Cited

U.S. PATENT DOCUMENTS

| | | | |
|---|---|---|---|
| 2,667,320 | A | 1/1954 | Whitley |
| 3,041,030 | A | 6/1962 | Heimrich |
| 3,064,931 | A | 11/1962 | Rowe |
| 3,208,706 | A | 9/1965 | Clark |
| 3,333,721 | A | 8/1967 | Marek |
| 3,347,507 | A | 10/1967 | Dyer |
| 3,817,448 | A | 6/1974 | Schneider |
| 3,869,979 | A | 3/1975 | Sulcek |
| 3,981,436 | A | 9/1976 | Neal |
| 4,338,987 | A | 7/1982 | Miles |
| 4,375,849 | A | 3/1983 | Hanifl |
| 4,420,168 | A | 12/1983 | Dewing |
| 4,466,538 | A | 8/1984 | Gianni |
| 4,488,643 | A | 12/1984 | Pepper |
| 4,494,652 | A | 1/1985 | Nelson et al. |
| 4,502,606 | A | 3/1985 | Shillington et al. |
| 4,520,926 | A | 6/1985 | Nelson |
| 4,576,281 | A | 3/1986 | Kirksey |
| 4,580,688 | A | 4/1986 | Harris et al. |
| 4,600,112 | A | 7/1986 | Shillington et al. |
| 4,637,545 | A | 1/1987 | Stewart |
| 4,657,139 | A | 4/1987 | Hanifl et al. |
| D292,037 | S | 9/1987 | Hanifl |
| D292,777 | S | 11/1987 | Shillington et al. |
| 4,715,498 | A | 12/1987 | Hanifl |
| 4,736,860 | A | 4/1988 | Bemis |
| 4,765,548 | A | 8/1988 | Sing |
| 4,779,728 | A | 10/1988 | Hanifl et al. |
| 4,809,850 | A | 3/1989 | Laible et al. |
| 4,842,138 | A | 6/1989 | Sandel et al. |
| D302,291 | S | 7/1989 | Heubel et al. |
| 4,863,057 | A | 9/1989 | Hanifl et al. |
| 4,867,309 | A | 9/1989 | Germain |
| 4,869,366 | A | 9/1989 | Bruno |
| D304,109 | S | 10/1989 | Hanifl |
| 4,874,103 | A | 10/1989 | Quisenberry et al. |
| 4,877,150 | A | 10/1989 | Otto et al. |
| 4,883,189 | A | 11/1989 | Lobbert |
| 4,886,164 | A | 12/1989 | Stein et al. |
| 4,892,191 | A | 1/1990 | Nakamura |
| 4,903,832 | A | 2/1990 | Stewart |
| D306,509 | S | 3/1990 | Hanifl et al. |
| 4,911,294 | A | 3/1990 | Russo et al. |
| 4,913,309 | A | 4/1990 | Fink |
| D307,841 | S | 5/1990 | Hanifl et al. |
| 4,930,631 | A | 6/1990 | Bruno |
| RE33,413 | E | 10/1990 | Hanifl |
| D311,334 | S | 10/1990 | Flynn et al. |
| 4,972,950 | A | 11/1990 | Shillington |
| 4,984,686 | A | 1/1991 | Shillington |
| 4,995,871 | A | 2/1991 | Sasaki et al. |
| 4,997,103 | A | 3/1991 | Daly |
| 5,005,729 | A | 4/1991 | Hollman |
| 5,014,874 | A | 5/1991 | Kitsos et al. |
| 5,024,326 | A | 6/1991 | Sandel et al. |
| 5,024,327 | A | 6/1991 | Shillington |
| 5,038,935 | A | 8/1991 | Wenkman et al. |
| 5,046,613 | A | 9/1991 | Baudry et al. |
| 5,048,712 | A | 9/1991 | Wolters |
| 5,058,764 | A | 10/1991 | Gaba |
| 5,062,828 | A | 11/1991 | Waltz |
| 5,065,939 | A | 11/1991 | Boothe et al. |
| 5,067,949 | A | 11/1991 | Freundlich et al. |
| 5,076,429 | A | 12/1991 | Patrick et al. |
| 5,076,458 | A | 12/1991 | Weiner et al. |
| 5,080,251 | A | 1/1992 | Noack |
| 5,082,132 | A | 1/1992 | Tsai |
| 5,090,564 | A | 2/1992 | Chimienti |
| 5,092,462 | A | 3/1992 | Sagstetter et al. |
| 5,094,358 | A | 3/1992 | Serio, Sr. |
| 5,097,950 | A | 3/1992 | Weiss et al. |
| 5,107,990 | A | 4/1992 | Wicherski et al. |
| D326,753 | S | 6/1992 | DeBusk |
| 5,127,522 | A | 7/1992 | Ranford |
| D328,810 | S | 8/1992 | Boothe et al. |
| 5,143,389 | A | 9/1992 | Jonkers |
| 5,145,063 | A | 9/1992 | Lee |
| 5,152,394 | A | 10/1992 | Hughes |
| 5,154,345 | A | 10/1992 | Shillington |
| 5,163,574 | A | 11/1992 | Sosan |
| 5,165,563 | A | 11/1992 | McKendry |
| 5,167,193 | A | 12/1992 | Withers et al. |
| D332,680 | S | 1/1993 | Ramirez |
| D332,852 | S | 1/1993 | Delmerico |
| 5,176,256 | A | 1/1993 | Sawaya |
| 5,178,322 | A | 1/1993 | Shillington |
| 5,183,156 | A | 2/1993 | Bruno |
| 5,184,720 | A | 2/1993 | Packer et al. |
| 5,188,598 | A | 2/1993 | Thead et al. |
| 5,193,678 | A | 3/1993 | Janocik et al. |
| 5,195,635 | A | 3/1993 | Cornwell |
| 5,195,649 | A | 3/1993 | Wolters |
| 5,199,973 | A | 4/1993 | Funk, Sr. |
| 5,201,417 | A | 4/1993 | Outlaw, III |
| 5,201,418 | A | 4/1993 | Hanlon |
| 5,230,525 | A | 7/1993 | Delmerico et al. |
| 5,235,795 | A | 8/1993 | DeBusk |
| 5,240,108 | A | 8/1993 | Tonna |
| 5,242,074 | A | 9/1993 | Conaway et al. |
| D341,237 | S | 11/1993 | DeBusk |
| 5,273,161 | A | 12/1993 | Sagstetter |
| 5,273,221 | A | 12/1993 | McCarthy |
| 5,275,280 | A | 1/1994 | Everhart |
| 5,281,391 | A | 1/1994 | Hanson et al. |
| 5,322,164 | A | 6/1994 | Richardson et al. |
| 5,323,901 | A | 6/1994 | Outlaw, III |
| 5,323,902 | A | 6/1994 | Palmer et al. |
| 5,337,911 | A | 8/1994 | Holub |
| 5,346,086 | A | 9/1994 | Harris |
| 5,348,222 | A | 9/1994 | Patey |
| 5,348,549 | A | 9/1994 | Brown et al. |
| D351,906 | S | 10/1994 | Marsh |
| 5,354,023 | A | 10/1994 | Meeks |
| D352,350 | S | 11/1994 | Rambo et al. |
| 5,372,271 | A | 12/1994 | Miller et al. |
| 5,385,105 | A | 1/1995 | Withers et al. |
| 5,386,910 | A | 2/1995 | Liss |
| 5,387,735 | A | 2/1995 | Ponsi et al. |
| 5,395,008 | A | 3/1995 | Bemis et al. |
| 5,402,887 | A | 4/1995 | Shillington |
| 5,409,113 | A | 4/1995 | Richardson et al. |
| D358,240 | S | 5/1995 | Mosior |
| 5,413,243 | A | 5/1995 | Bemis et al. |
| 5,415,315 | A | 5/1995 | Ramirez |
| 5,417,659 | A | 5/1995 | Gaba |
| 5,419,435 | A | 5/1995 | Perzan et al. |
| D360,062 | S | 7/1995 | Mosior |
| 5,433,412 | A | 7/1995 | Watt et al. |
| D362,502 | S | 9/1995 | Anderson et al. |
| 5,458,072 | A | 10/1995 | Hughes et al. |
| 5,465,841 | A | 11/1995 | Wilson et al. |
| 5,474,180 | A | 12/1995 | Robinson et al. |
| 5,474,181 | A | 12/1995 | Shillington et al. |
| 5,474,201 | A | 12/1995 | Liu |
| 5,474,341 | A | 12/1995 | Putman et al. |
| 5,494,158 | A | 2/1996 | Erickson |
| 5,494,186 | A | 2/1996 | Marsh |
| 5,495,941 | A | 3/1996 | Leonard |
| 5,507,408 | A | 4/1996 | Mosior et al. |
| 5,531,346 | A | 7/1996 | Mosior |
| 5,531,348 | A | 7/1996 | Baker et al. |
| 5,538,158 | A | 7/1996 | Prout et al. |
| 5,560,512 | A | 10/1996 | Hahn |
| 5,570,547 | A | 11/1996 | Webb et al. |
| 5,570,783 | A | 11/1996 | Thorne et al. |
| 5,582,322 | A | 12/1996 | Prout et al. |
| 5,603,404 | A | 2/1997 | Nazare et al. |
| 5,605,245 | A | 2/1997 | Bemis et al. |
| 5,630,506 | A | 5/1997 | Thorne et al. |
| 5,647,502 | A | 7/1997 | Marsh |
| 5,651,231 | A | 7/1997 | Garland |
| 5,659,247 | A | 8/1997 | Clements |
| 5,671,859 | A | 9/1997 | Sheu et al. |
| D385,349 | S | 10/1997 | Mosior et al. |

(56) References Cited

U.S. PATENT DOCUMENTS

D385,626 S 10/1997 Mosior et al.
5,673,811 A 10/1997 Dickinson et al.
5,690,242 A 11/1997 Campbell, Jr.
D388,577 S 12/1997 Rehrig et al.
5,724,226 A 3/1998 Ruch et al.
5,730,451 A 3/1998 Walker
D393,334 S 4/1998 Presnell et al.
5,740,909 A 4/1998 Nazare et al.
5,765,339 A 6/1998 Garland
5,769,006 A 6/1998 Allaer
D403,241 S 12/1998 Nask et al.
5,848,692 A 12/1998 Thorne et al.
D404,483 S 1/1999 Harwood et al.
5,879,337 A 3/1999 Kuracina et al.
5,890,615 A 4/1999 Petras
5,899,468 A 5/1999 Apps et al.
5,901,872 A 5/1999 Zollinhofer et al.
5,901,874 A 5/1999 Deters
D411,008 S 6/1999 Gaba et al.
5,918,762 A 7/1999 Gaba et al.
5,947,285 A * 9/1999 Gaba .................... A61B 50/362
206/370
D414,864 S 10/1999 Gaba et al.
D415,273 S 10/1999 Gaba et al.
5,967,317 A 10/1999 Wright
5,984,137 A 11/1999 Grosjean
6,001,080 A 12/1999 Kuracina et al.
6,010,024 A 1/2000 Wang
D421,122 S 2/2000 Gaba et al.
6,053,354 A 4/2000 Diemeyer
6,062,001 A 5/2000 Kunik
6,070,751 A 6/2000 Mejias
D429,864 S 8/2000 Schmidt
D431,079 S 9/2000 Crawford
6,120,743 A 9/2000 Papari
6,138,558 A 10/2000 Harrington
D438,964 S 3/2001 Gaba et al.
6,202,922 B1 3/2001 Phillips et al.
6,250,465 B1 6/2001 Daniels et al.
D445,228 S 7/2001 Apps et al.
6,253,916 B1 7/2001 Bickel
D447,233 S 8/2001 Bickel et al.
6,283,909 B1 9/2001 Sharp
6,286,675 B1 9/2001 Schmidt
D451,195 S 11/2001 Daniels et al.
D451,255 S 11/2001 Schmidt
D452,944 S 1/2002 Schmidt
6,341,438 B1 1/2002 Sianos
6,435,729 B1 8/2002 Thevenod et al.
6,443,929 B1 9/2002 Kuracina et al.
6,460,453 B1 10/2002 Frauenfeld
6,540,098 B1 4/2003 Jarvas et al.
6,561,352 B2 5/2003 Sherman et al.
D478,663 S 8/2003 Moats et al.
D478,664 S 8/2003 Moats et al.
D478,701 S 8/2003 Panek, Jr.
6,612,457 B1 9/2003 Caron
6,623,316 B1 9/2003 Wu
6,626,316 B2 9/2003 Yang
6,626,321 B2 9/2003 Jaeger
6,651,992 B1 11/2003 Smith, Sr.
D485,906 S 1/2004 Danssaert et al.
6,691,867 B1 2/2004 Bickel et al.
6,712,207 B2 3/2004 Panek, Jr. et al.
6,722,672 B2 4/2004 Cates et al.
6,761,283 B1 7/2004 Gilliam et al.
6,889,831 B2 5/2005 Pike
D518,173 S 3/2006 Coates
D531,309 S 10/2006 Bennett
7,114,629 B2 10/2006 Panek, Jr.
7,119,689 B2 10/2006 Mallett et al.
7,123,150 B2 10/2006 Mallett et al.
7,126,480 B2 10/2006 Mallett et al.
7,138,918 B2 11/2006 Mallett et al.
D538,499 S 3/2007 Schmidt
7,192,037 B1 3/2007 Peña
D545,521 S 6/2007 Titas et al.
7,243,792 B2 7/2007 Panek, Jr. et al.
7,275,645 B2 10/2007 Mallett et al.
7,296,688 B2 11/2007 Mallett et al.
D556,545 S 12/2007 Titas et al.
7,303,080 B2 12/2007 Mallett et al.
7,303,081 B2 12/2007 Mallett et al.
7,303,082 B2 12/2007 Mallett et al.
7,311,207 B2 12/2007 Mallett et al.
D560,489 S 1/2008 Satnick
7,318,529 B2 1/2008 Mallett et al.
7,341,147 B2 3/2008 Mallett et al.
7,364,049 B2 4/2008 Panek, Jr.
D569,074 S 5/2008 Irwin et al.
7,383,195 B2 6/2008 Mallett et al.
7,392,903 B2 7/2008 Jolley et al.
D575,061 S 8/2008 Titas et al.
7,445,116 B2 11/2008 Dansaert et al.
7,454,358 B2 11/2008 Mallett et al.
7,483,837 B2 1/2009 Mallett et al.
7,487,100 B2 2/2009 Mallett et al.
7,513,363 B2 4/2009 Brown et al.
7,516,844 B2 4/2009 Erickson et al.
D591,859 S 5/2009 Stark et al.
7,533,028 B2 5/2009 Mallett et al.
7,533,029 B2 5/2009 Mallett et al.
7,534,392 B1 5/2009 Kodis
7,534,405 B1 5/2009 Kodis
7,562,025 B2 7/2009 Mallett et al.
7,565,299 B2 7/2009 Mallett et al.
7,596,844 B2 10/2009 Japuntich et al.
7,597,681 B2 10/2009 Sutton et al.
7,600,638 B2 10/2009 Finnestad et al.
7,600,639 B2 10/2009 Japuntich et al.
7,617,113 B2 11/2009 Mallett et al.
7,620,559 B2 11/2009 Mallett et al.
7,660,724 B2 2/2010 Mallett et al.
7,664,656 B2 2/2010 Mallett et al.
7,694,811 B2 4/2010 Brown et al.
7,694,822 B2 4/2010 Sullivan et al.
7,699,247 B2 4/2010 Kodis
7,775,387 B2 8/2010 Lipton et al.
7,776,262 B1 8/2010 Kodis
7,784,167 B2 8/2010 Panek, Jr.
7,789,230 B2 9/2010 Klein
7,815,046 B2 10/2010 Sansoucy et al.
7,877,849 B2 2/2011 Panek, Jr. et al.
7,898,201 B2 3/2011 Fisher et al.
7,931,878 B2 4/2011 Kodis
7,937,814 B2 5/2011 Voit
7,970,722 B1 6/2011 Owen et al.
7,971,715 B1 7/2011 Fernandes et al.
7,980,408 B2 7/2011 Japuntich et al.
8,005,777 B1 8/2011 Owen et al.
8,038,025 B2 10/2011 Stark et al.
8,096,414 B2 1/2012 Finnestad et al.
D655,061 S 2/2012 Scaturro
8,113,349 B2 2/2012 Sansoucy et al.
8,160,988 B1 4/2012 Owen et al.
8,162,139 B2 4/2012 Iske
8,172,859 B2 5/2012 Matsuno et al.
8,195,328 B2 6/2012 Mallett et al.
8,201,323 B2 6/2012 Miller et al.
8,204,620 B2 6/2012 Mallett et al.
8,209,918 B1 7/2012 Voit
8,296,243 B2 10/2012 Mallett et al.
8,324,443 B2 12/2012 Kunik et al.
8,393,488 B2 3/2013 Japuntich et al.
8,584,885 B2 11/2013 Finnestad et al.
2002/0158068 A1 10/2002 Panek
2003/0213714 A1 11/2003 Moats et al.
2004/0020927 A1 2/2004 Yang et al.
2006/0070898 A1 4/2006 Dansaert et al.
2009/0108007 A1 4/2009 Anderson et al.
2011/0024414 A1 2/2011 Widmer

(56) References Cited

U.S. PATENT DOCUMENTS

| | | | |
|---|---|---|---|
| 2012/0024878 | A1 | 2/2012 | Kelly et al. |
| 2012/0037626 | A1 | 2/2012 | Finnestad |

FOREIGN PATENT DOCUMENTS

| | | | |
|---|---|---|---|
| DE | 2740335 | | 3/1979 |
| DE | 3908186 | | 3/1990 |
| EP | 541339 | A2 | 5/1993 |
| EP | 527938 | | 3/1996 |
| EP | 842641 | A1 | 5/1998 |
| EP | 1447109 | A2 | 8/2004 |
| EP | 1609432 | A1 | 12/2005 |
| EP | 1709925 | A1 | 10/2006 |
| EP | 2057958 | A2 | 5/2009 |
| FR | 2730919 | A1 | 8/1996 |
| FR | 2746931 | A1 | 10/1997 |
| FR | 2759064 | A1 | 8/1998 |
| FR | 2766799 | A1 | 2/1999 |
| GB | 2040268 | A | 8/1980 |
| GB | 2277247 | A | 10/1994 |
| GB | 2388032 | A | 11/2003 |
| GB | 2398225 | A | 8/2004 |
| GB | 2447008 | A | 9/2008 |
| NL | 1003928 | C2 | 3/1998 |
| WO | 1988008399 | A1 | 11/1988 |
| WO | 1991001920 | A2 | 2/1991 |
| WO | 1991017095 | A1 | 11/1991 |
| WO | 1991017099 | A1 | 11/1991 |
| WO | 1993009039 | A1 | 5/1993 |
| WO | 1994021538 | A1 | 9/1994 |
| WO | 1995003076 | A1 | 2/1995 |
| WO | 1995033417 | A2 | 12/1995 |
| WO | 1996006024 | A1 | 2/1996 |
| WO | 1996009228 | A1 | 3/1996 |
| WO | 1996020880 | A1 | 7/1996 |
| WO | 1996025894 | A1 | 8/1996 |
| WO | 1996031414 | A1 | 10/1996 |
| WO | 1997037413 | A1 | 10/1997 |
| WO | 1998034855 | A1 | 8/1998 |
| WO | 1998057869 | A1 | 12/1998 |
| WO | 1999059659 | A1 | 11/1999 |
| WO | 2000042938 | A1 | 7/2000 |
| WO | 2003091710 | A1 | 11/2003 |
| WO | 2005120610 | A2 | 12/2005 |
| WO | 2006119247 | A1 | 11/2006 |
| WO | 2007038133 | A1 | 4/2007 |
| WO | 2008036218 | A2 | 3/2008 |
| WO | 2009055661 | A2 | 4/2009 |

* cited by examiner

SHARPS CONTAINER

RELATED APPLICATIONS

The present invention is a continuation of U.S. patent application Ser. No. 18/099,163 filed Jan. 19, 2023, now U.S. Pat. No. 12,082,951 issued Sep. 10, 2024, which is a continuation of U.S. patent application Ser. No. 16/845,842 filed Apr. 10, 2020, now U.S. Pat. No. 11,559,369 issued Jan. 24, 2023, which is a continuation of U.S. patent application Ser. No. 16/436,920 filed Jun. 11, 2019, now U.S. Pat. No. 10,617,485 issued Apr. 14, 2020, which is a continuation of U.S. patent application Ser. No. 14/921,586 filed Oct. 23, 2015, now U.S. Pat. No. 10,321,968 issued Jun. 18, 2019, which applications are incorporated herein by reference in their entirety.

FIELD OF THE INVENTION

The present invention relates generally to containers for disposal of medical waste, and in particular to the disposal of contaminated items. The present invention may be a disposal system for use in a hospital or similar environment where contaminated items must be collected and disposed of without creating a hazard for patients or hospital personnel.

BACKGROUND OF THE INVENTION

In hospitals, clinics and similar institutions, contamination is of utmost concern. Disposable, single use patient-care products, which used to be the exception, are now the norm. Such hospital waste products might include surgical sharps, such as needles, syringes, scalpel blades, or the like, or might include gauzes, bandages, or sponges.

Various types of containers for hospital use have been developed for receiving medical waste in a surgical operating room, pre-op or post-op room, or a patient's room. These containers are particularly designed to protect the user of such containers, such as doctors, nurses, or other hospital personnel, from the hospital waste products that may be disposed therein.

The proximal disposal of sharps in patient rooms has spawned a host of specialized sharps disposal containers. These containers are primarily designed to allow for the easy disposal of sharps in a manner that does not require excess effort, exposure to the sharp portion of a device and in which the disposed of sharp cannot be subsequently accessed. In most instances, the disposal system consists of a non-disposable cabinet or support that is more or less permanently affixed to a room surface (usually affixed to the wall with some type of anchor) and a disposable container that fits within or is attached to the cabinet or support. Typically, the disposable container utilizes some type of door that prevents unobstructed access to the interior of the container, but allows relatively easy disposal of the sharp.

It is important to prevent the user of a sharps container from being accidentally cut or punctured by its contents. Furthermore, it is important to prevent access to the contents of the container during disposal thereof.

Sharps containers have commonly been provided with a relatively large circular opening through which sharps may be dropped in a vertical orientation for haphazard collection within the container. As the container fills, the user runs the risk of a previously inserted sharp protruding from the opening where it can stab the hand of the next operator inserting something into the container. Side walls may be constructed of relatively soft or thin-walled material which could be pierced by any one of the haphazardly arranged needles within the container thereby possibly exposing to infectious disease the next person brushing against the container. Other known sharps containers have a mailbox-like structure having a tilt pan which tips outwardly for receiving a sharp and which tips inwardly for depositing the sharp in the container. In this manner, the interior of the container is never completely open to the room and the sharp can be disposed of with one simple motion.

However, previous designs have been subject to jamming, improper function and manufacturing difficulties. For example, previous designs included lids with multiple distinct parts. In some examples, these parts may be ultrasonically welded together. This creates extra manufacturing steps as well as unnecessarily using more plastic.

DETAILED DESCRIPTION

Figure 1:
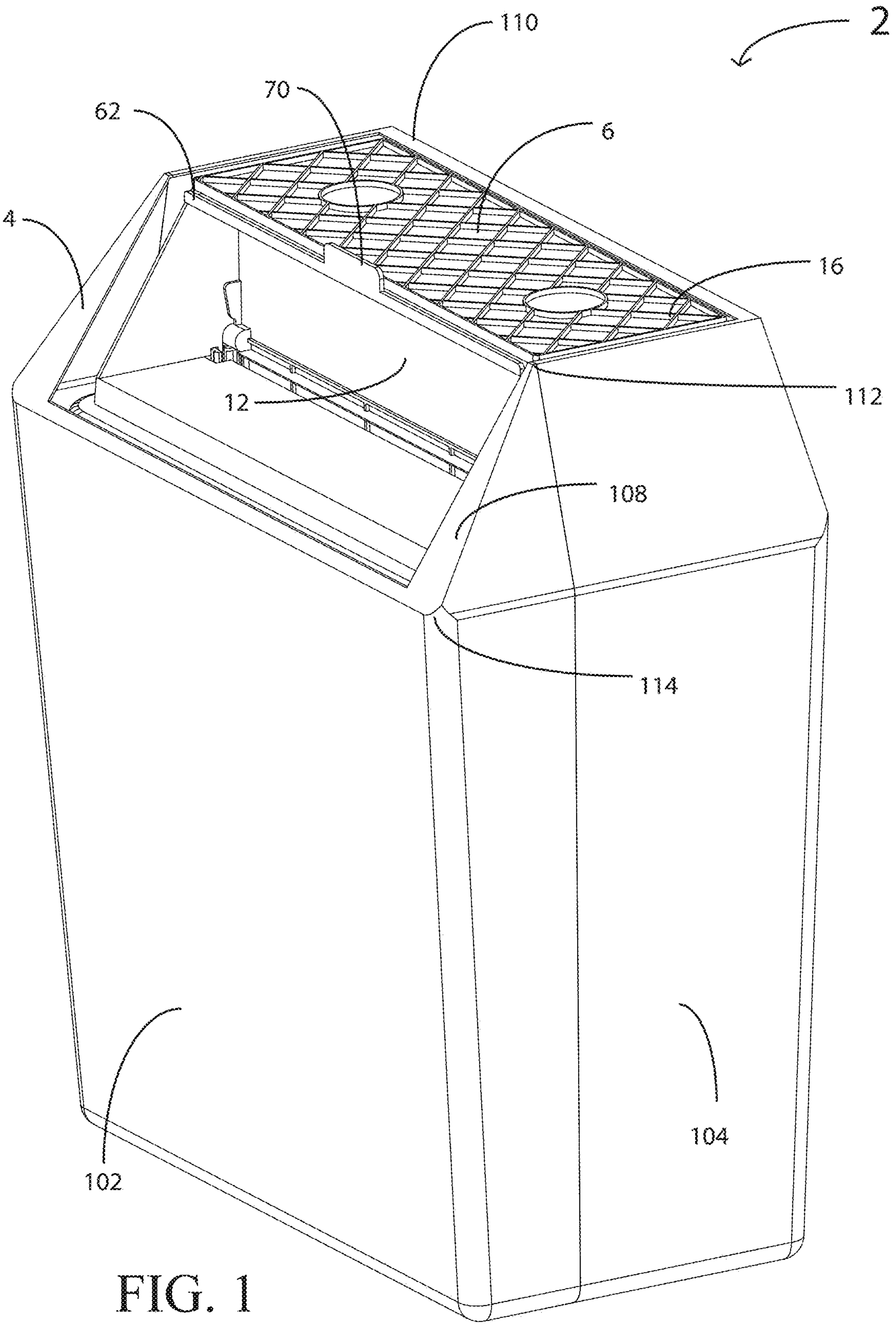
FIG. 1 is a side perspective view of a sharps disposal system including a permanent exterior cabinet and disposable interior container.
Figure 2:
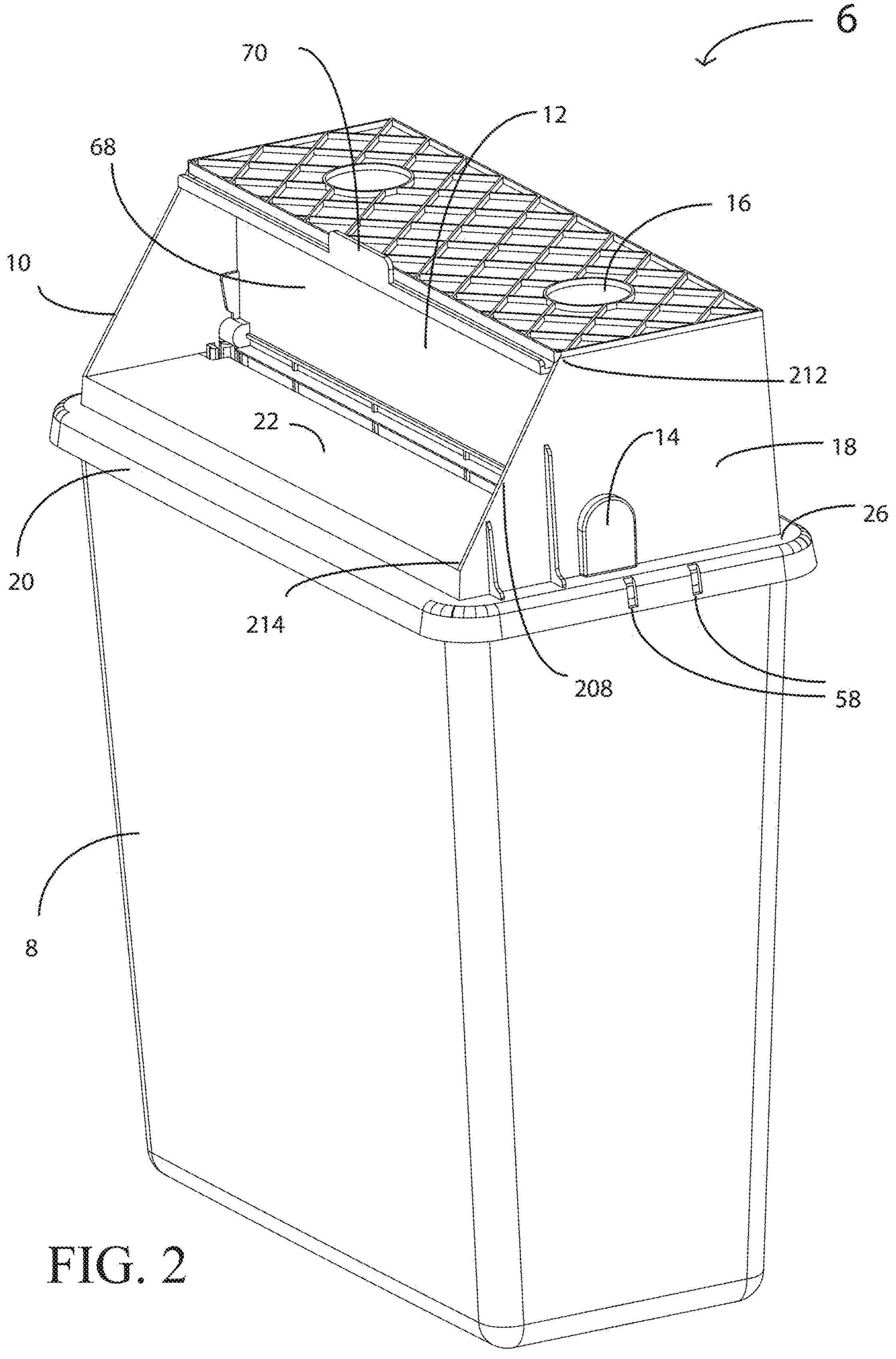
FIG. 2 is a side perspective view of the disposable interior container with the closure flap in a closed position.

With reference to FIGS. 1-2, the disposal system 2 of the present invention includes a locking exterior cabinet 4 that may be wall mounted and a disposable container 6 that is placed within the cabinet 4. For example, as shown in FIG. 1, the cabinet 4 includes a bottom wall, rear wall 110, opposite upstanding side walls 104 and a front wall 102. The front wall 102 may be hinged to the side wall 104 or to the bottom wall such that the front wall can be swung open to remove the disposable container 6 from the cabinet 4. The front wall 102 or corresponding side wall 104 may include a locking mechanism (not shown) for securely locking a disposable container 6 into the cabinet 4. The locking mechanism may comprise a locking tab or latch, or it may include a keyed lock.

The cabinet 4 may be secured to a wall, desk, table or other surface. The securing mechanism may consist of screws or other fasteners inserted through the cabinet into the surface that are only accessible when the cabinet 4 is opened and the container 6 is removed. In this way, the cabinet could only be removed from the surface by someone with access to a cabinet key. Alternatively, an exterior frame, locking tabs or other mechanism may be provided to attach the cabinet to the surface.

As further shown in FIG. 1, embodiments of the cabinet 4 may not include a top wall. Rather, the cabinet side walls 104 and rear wall 110 may extend to and generally parallel to or below a top surface 16 of the container 6. Alternatively, the cabinet may include a top wall that is dimensioned so as not to interfere with movement of a closure flap 12 of the container 6. The front wall 102 of the cabinet 4 may have an angled or sloped portion 108. The sloped portion 108 may be angled such that the top end portion 112 of the sloped portion 108 aligns generally with an upper portion 62 of the closure flap 12 when the closure flap 12 is in a closed and locked position, and the bottom end portion 114 of the sloped portion 108 aligns below an upper portion 62 of the closure flap 12 when the closure flap is in an open position.

Figure 3:
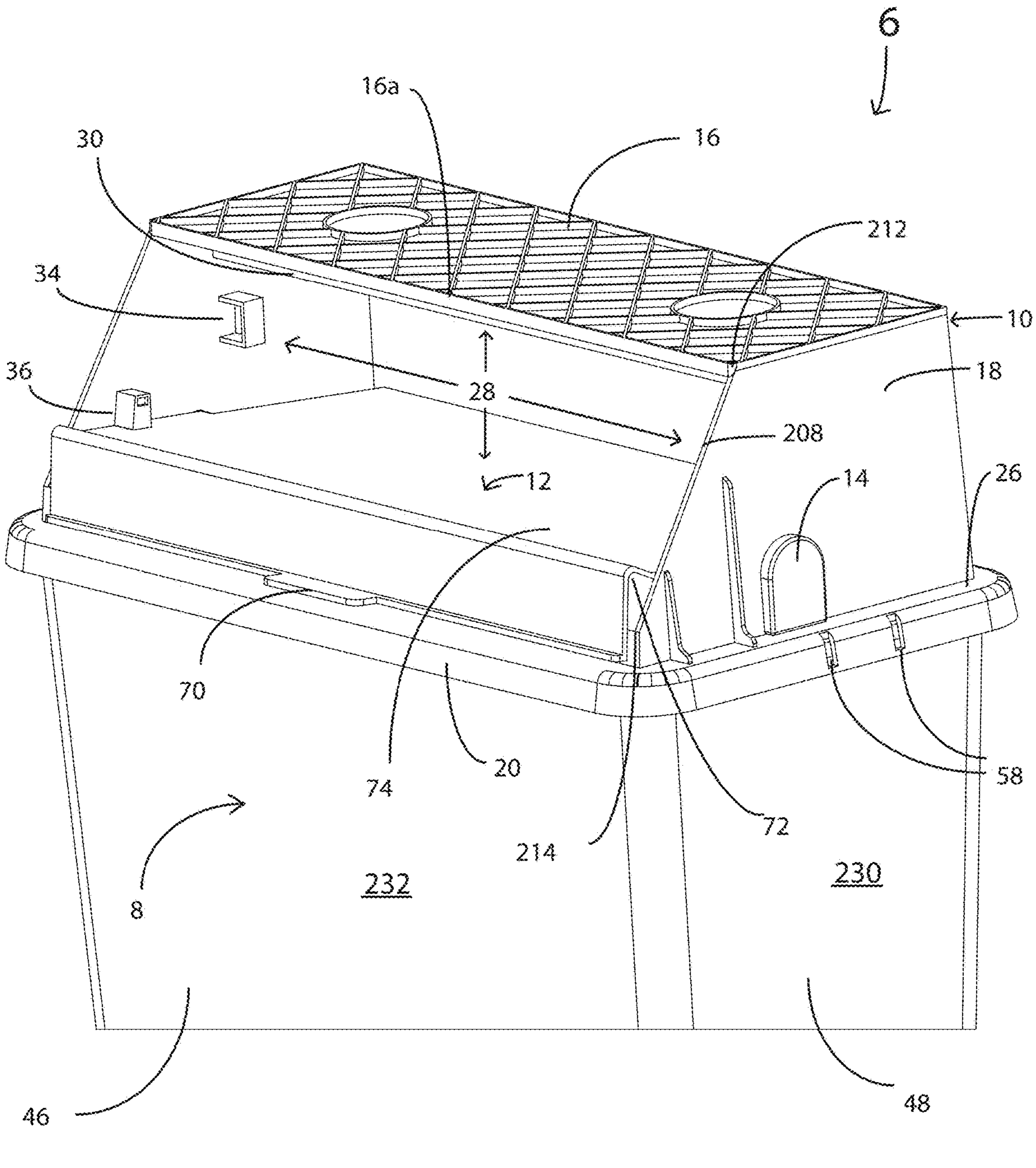
FIG. 3 is a front perspective view of the disposable interior container with the closure flap in an opened position.
Figure 4:
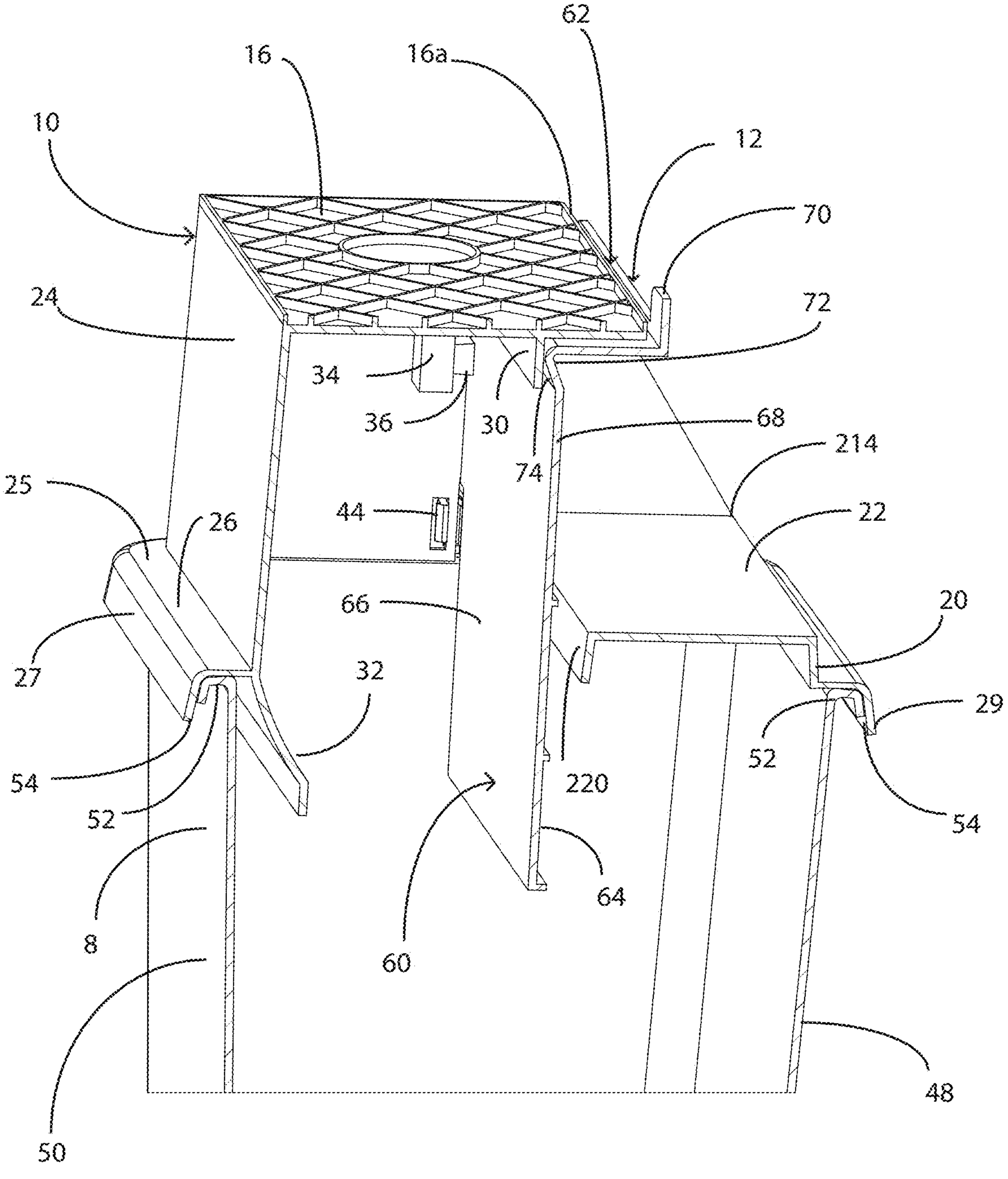
FIG. 4 is a side cut-away view of the interior of the disposable container with the closure flap in a closed and locked position.

As show in FIGS. 2-4, the disposable container 6 is preferably formed of four component parts including an open topped receptacle 8 for receiving medical waste, a snap fit lid 10, a pivotal closure flap 12 and a plurality of snap fit covers 14. The front portions of the lid side wall 18 may include a sloped portion 208 that generally corresponds with the sloped portion 108 of the cabinet front wall 102. Similarly, the sloped portion 208 may be angled such that the top portion 212 of the sloped portion 208 aligns generally with an upper portion 62 of the closure flap 12 when the closure flap 12 is in a closed and locked position, and the bottom end portion 214 of the sloped portion 208 aligns below an upper portion 62 of the closure flap 12 when the closure flap 12 is in an open position. The front shelf 22 provides a deck upon which the closure flap 12 may rest when in the open position.

As shown in FIGS. 3-4, the lid 10 includes an upper wall 16, side walls 18, a front wall 20, a front shelf 22, a rear wall 24, and a skirt 26 extending around the lower portions of the lid 10 side and rear walls 18, 24. Located in spaced relation between the front shelf 22, the front portion **16*a* of the upper wall 16 and front portion of the side walls 18, an elongated opening 28 is provided for receiving the closure flap 12 which is pivotally operable between a normal closed position, a fully opened position and a permanently closed and locked position. The closure flap is sized such that when is in the normal closed position, the lower portion 60 of the closure flap 12 extends into the receptacle 8 in spaced relation with the bottom wall (not shown) of the receptacle 8 and the upper portion 62 of the closure flap 12 extends above the lid upper wall 16. Still further, the closure flap is sized such that when in the open position, the lower portion 60 of the closure flap 12 sweeps immediately adjacent to the interior rear wall 24 of the lid 10 and the detent 72 of the upper portion of the closure flap approximately corresponds with the portion of the lid 10 where the front wall 20 and the front shelf 22** meet.

Figure 11:
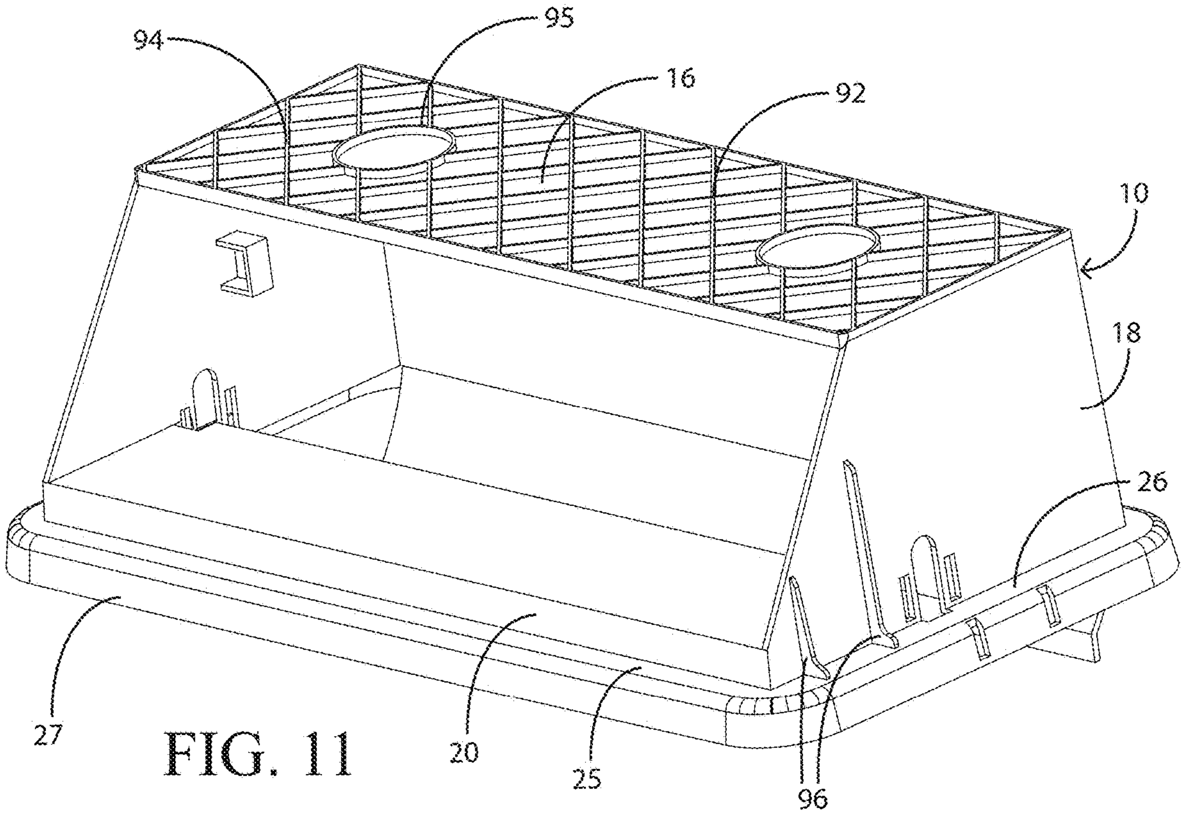
FIG. 11 is a perspective view of a lid of a disposable interior container.

The upper wall 16 of the lid 10 may have a generally planar and smooth surface as illustrated in FIG. 3. Alternatively, as shown in FIG. 11, embodiments of the lid 10 may include an upper wall 16 that incorporates one or more decorative or structural features. For example, the upper wall 16 may incorporate ribs 92 that increase the structural rigidity of the upper wall. These ribs may be formed in a cross-hatch pattern 94 or a circular pattern 95, or some combination of these or other patterns as may be appropriate to enhance the structure and/or aesthetics of the upper wall. Additionally, the lid 10 may incorporate ribs 96 that bridge the gap between the side wall 18 and the lid skirt 26 in order to provide additional structural integrity to the lid.

Figure 12:
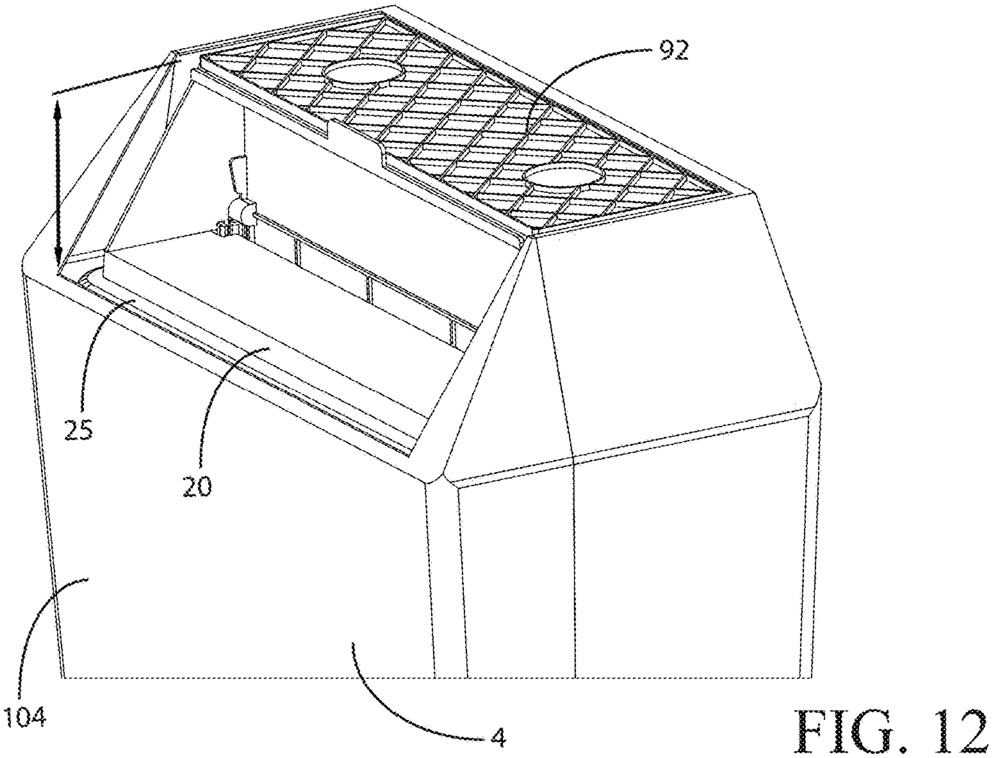
FIG. 12 is a perspective view of a sharps disposal system including a permanent exterior cabinet and disposable interior container.

As shown in FIG. 4, the skirt 26 may include a horizontal portion 25 that extends from the lid side 18 and rear walls 24. The skirt may also include a vertical portion 27 that extends below a flange 52 of the receptacle 8. In some embodiments, as illustrated in FIG. 4, the skirt 26 may not include a horizontal portion adjacent to the front wall 20. And the skirt 26 may generally vertically from the edge of the front shelf 22 to a lower edge 29 of the skirt. Alternatively, as illustrated in FIGS. 11-12, embodiments of the lid 10 may include a skirt horizontal portion 25 that extends adjacent to the front wall 20 in addition to the side walls 18 and rear wall. This horizontal portion 25 may be positioned such that it accommodates the geometry of the front wall 104 of the cabinet 4. For example, a top edge of the cabinet front wall 104 may include a lip that extends partially over the horizontal portion of the skirt 26.

Figure 5:
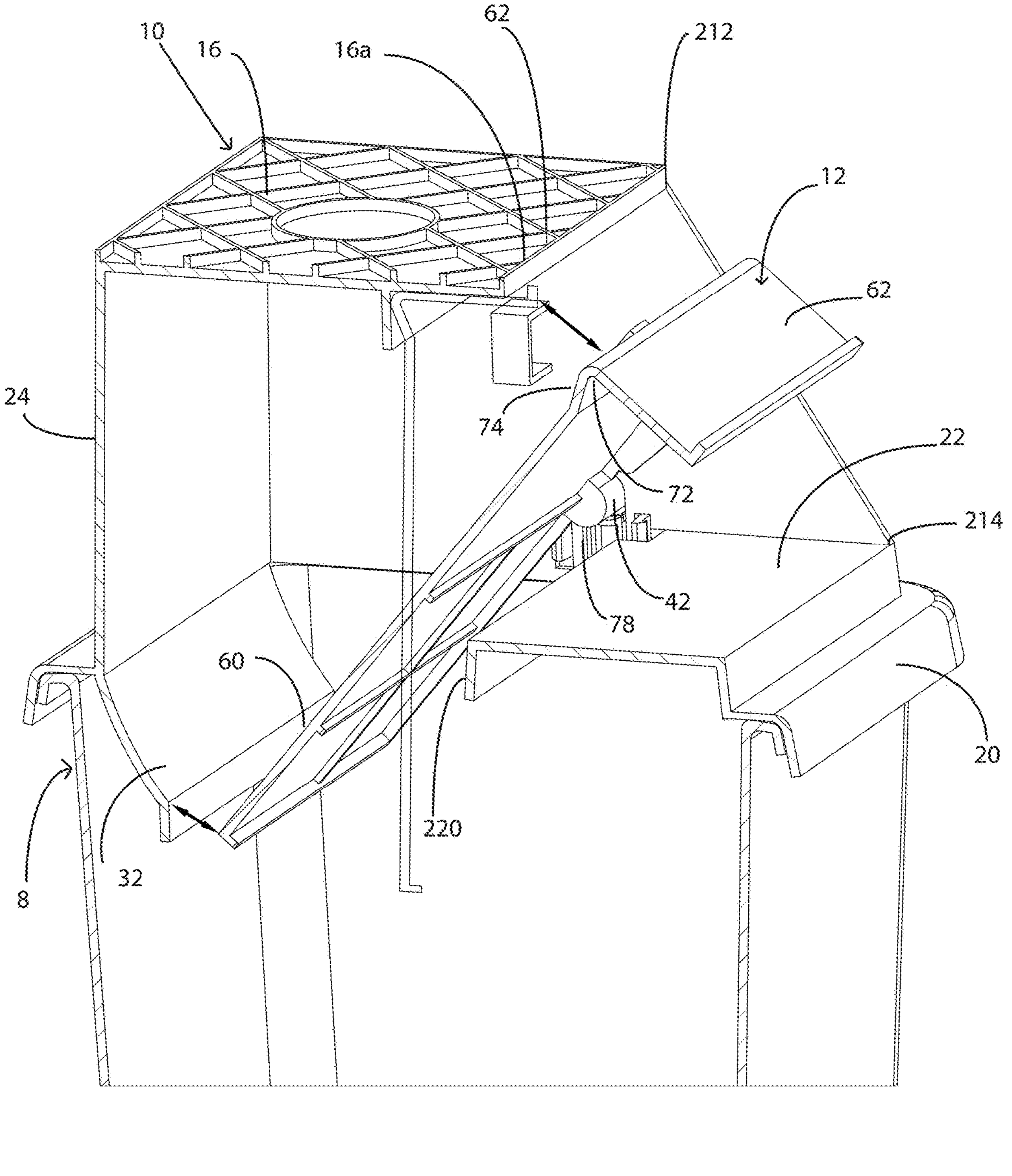
FIG. 5 is a side cut-away view of the interior of the disposable container with the closure flap in a partially open position.
Figure 6:
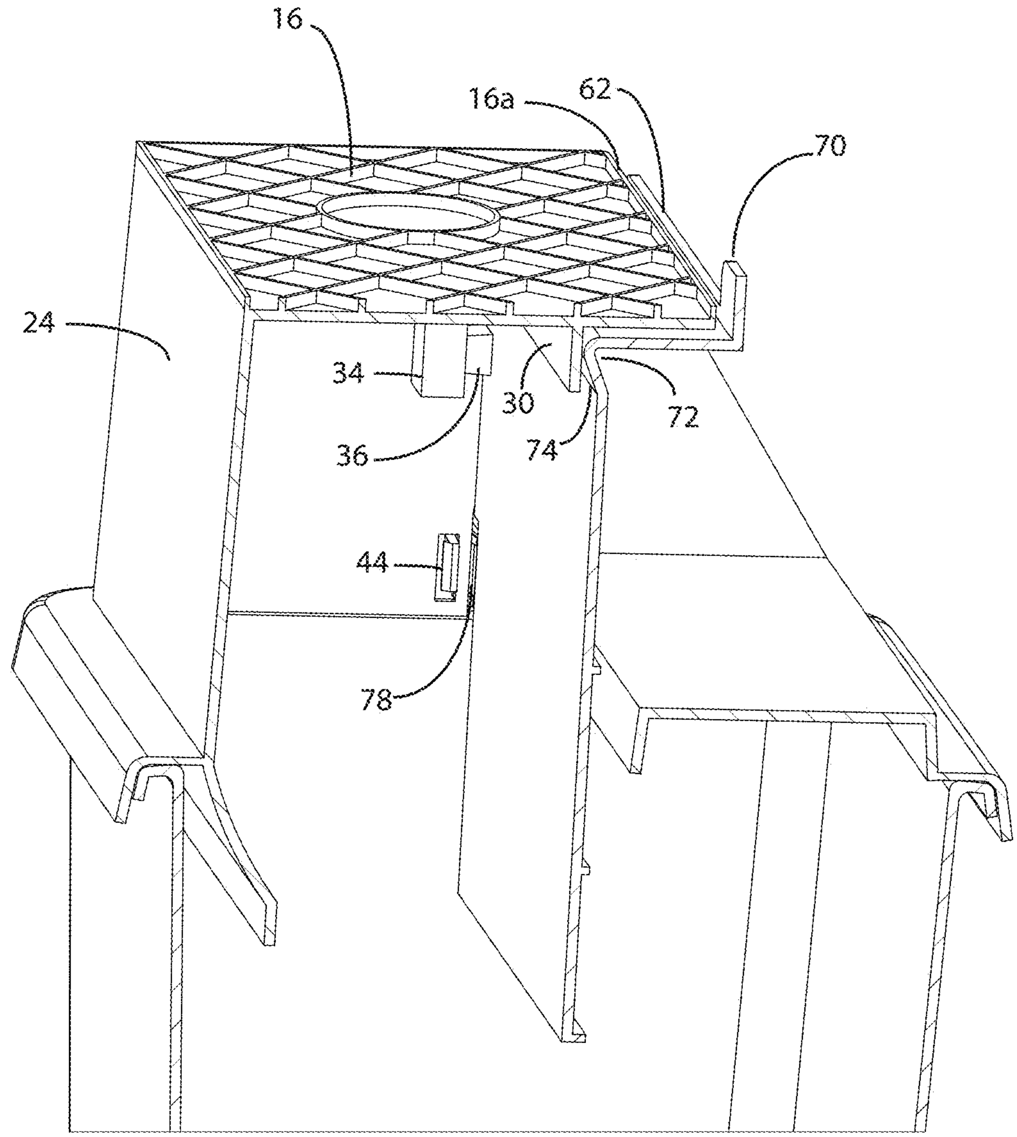
FIG. 6 is a side cut-away view of the interior of the disposable container with the closure flap in a closed and permanently locked position.

Turning to the interior surfaces of the lid 10, a plurality of features are provided to protect the user from accidental exposure to medical waste located within the receptacle 8. As shown in FIGS. 4-7 the front portion **16*a* of upper wall 16 interior, in spaced relation with the opening 28, includes a downward projection 30. As shown in FIGS. 4 and 5, the rear wall 24 interior includes a fixed cowl 32 which extends downwardly into the receptacle 8 to assist in guiding horizontally disposed sharps placed on the closure flap 12 into the receptacle 8. The projection 30 and the cowl 32 restrict access into the interior of the container 6 when the closure flap 12 is in a fully open position by constricting access within the area that is the opening 28. The relative spacing of the front shelf 22, the downward projection 30 and the cowl 32 define a limited opening 28 which restricts access to the interior of the container 6. The relative spacing of these features are dimensioned so that access to the interior of the container 6 is inhibited to the extent that it is difficult or impossible for an adult human hand to pass through the opening 28. Still further, once the closure flap 12 is locked in a fully closed position, if the closure flap 12 is pried away from the front portion 16*a* of the lid upper wall 16 in an attempt to gain access to the interior of the container 6, the projection 30** offers a further safety feature by restricting access to the interior of the container.

The front shelf 22 includes a front portion that aligns with the front wall 20 and a rear portion that includes a projection 220, which is directed downward into the interior of the receptacle 8. When the closure flap 12 is in a closed position, the medial portion of the closure flap rests against the downward projection 220. As with other lid interior features, downward projection 220 assists in restricting access into the interior of the contain 6 by providing structural support to the front shelf 22, as well as offers a further safety feature by restricting access to the interior of the container 6 in the event an attempt to pry open the closure flap 12 is made in an attempt to gain access to the interior of the container Additionally, in spaced relation with the interior upper wall 16 the interior side walls 18 are provided a plurality of slots 34 through which hooks 36 of the closure flap 12 are inserted to provide permanent closure of the container 6 for transport and disposal. Once the hooks 36 pass through the slots 34, movement of the closure flap 12 is blocked so that force applied against the closure flap 12 will not move the closure flap 12 from a closed position to an open position.

Figure 8:
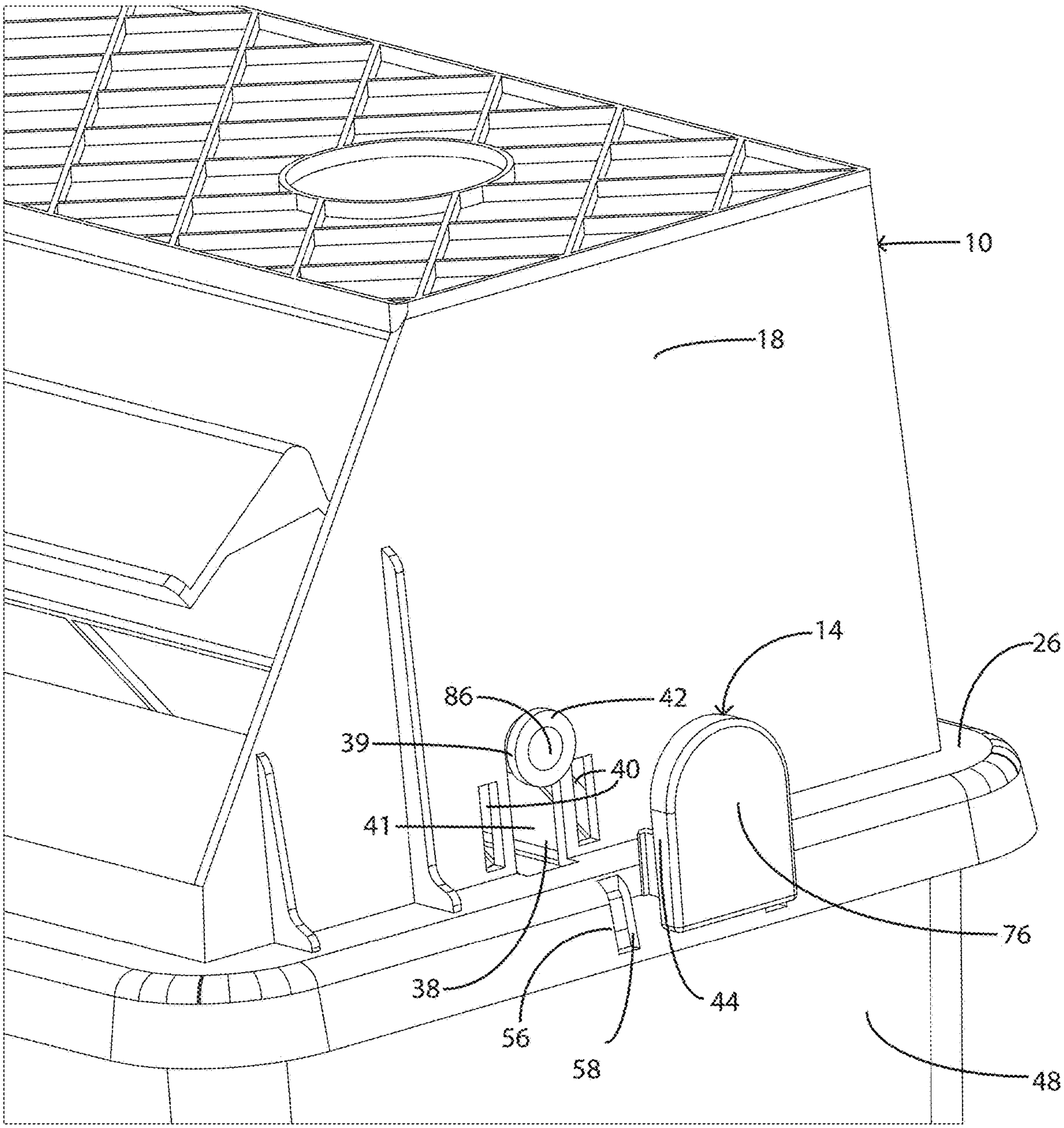
FIG. 8 is a partially exploded side perspective view of the lid of the disposable container.

As shown in FIG. 8, the lid 10 may also include an opening 38 through which an axial hub 42 of the closure flap 12 may be inserted. In addition, the lid may include openings 40 through which locking tabs 44 of the snap fit cover 14 extend, as discussed in greater detail below.

The receptacle 8 includes a bottom wall, front wall 46, rear wall 48 and side walls 50. As shown in FIG. 4, the upper portions of the receptacle 8 front, rear and side walls, 46, 48, 50 include a flange 52 that extends outwardly and downwardly from the top edge of the side walls. The flange is adapted to receive corresponding inwardly extending locking fingers 54 of the lid skirt 26 to provide a permanent snap fit connection between the lid 10 and receptacle 8.

Figure 9:
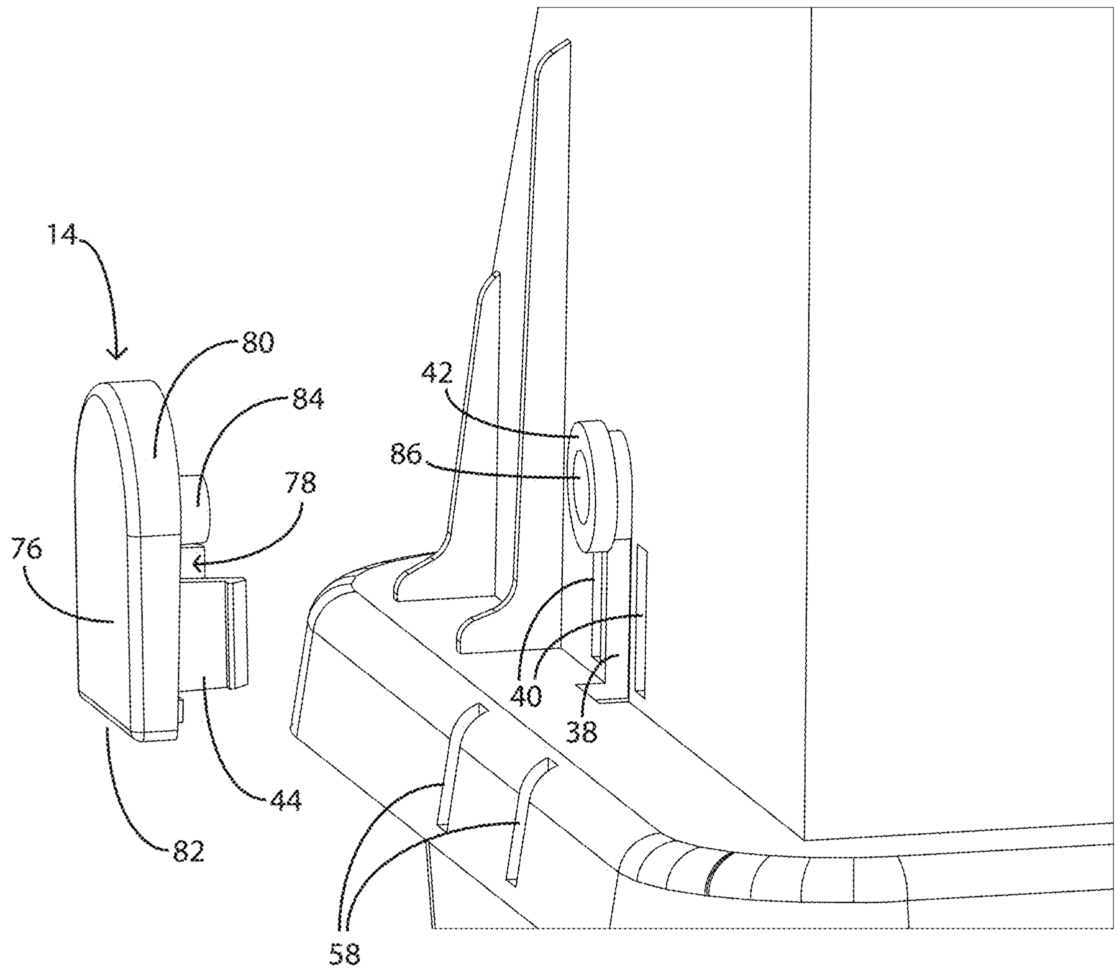
FIG. 9 is an exploded side perspective view of the lid and component parts of the disposable container.

As shown in FIGS. 8-9, the upper edges of the receptacle 8 side walls 48 may include locking fingers 56 that are inserted into through openings 58 located on the lid 10 side wall skirt 26 permanent provide a snap fit connection between the receptacle 8 and lid 10.

Additional embodiments of the disposal system may include viewing ports in the one or more of the front 102 and side 104 walls of the cabinet 4. These view ports correspond to view ports 230, 232 (FIG. 3) that may be located in the front 46 and side 50 walls of the receptacle 8. The viewing ports permit a user to view the contents of the system and determine empty/full status prior to attempted use.

Figure 7:
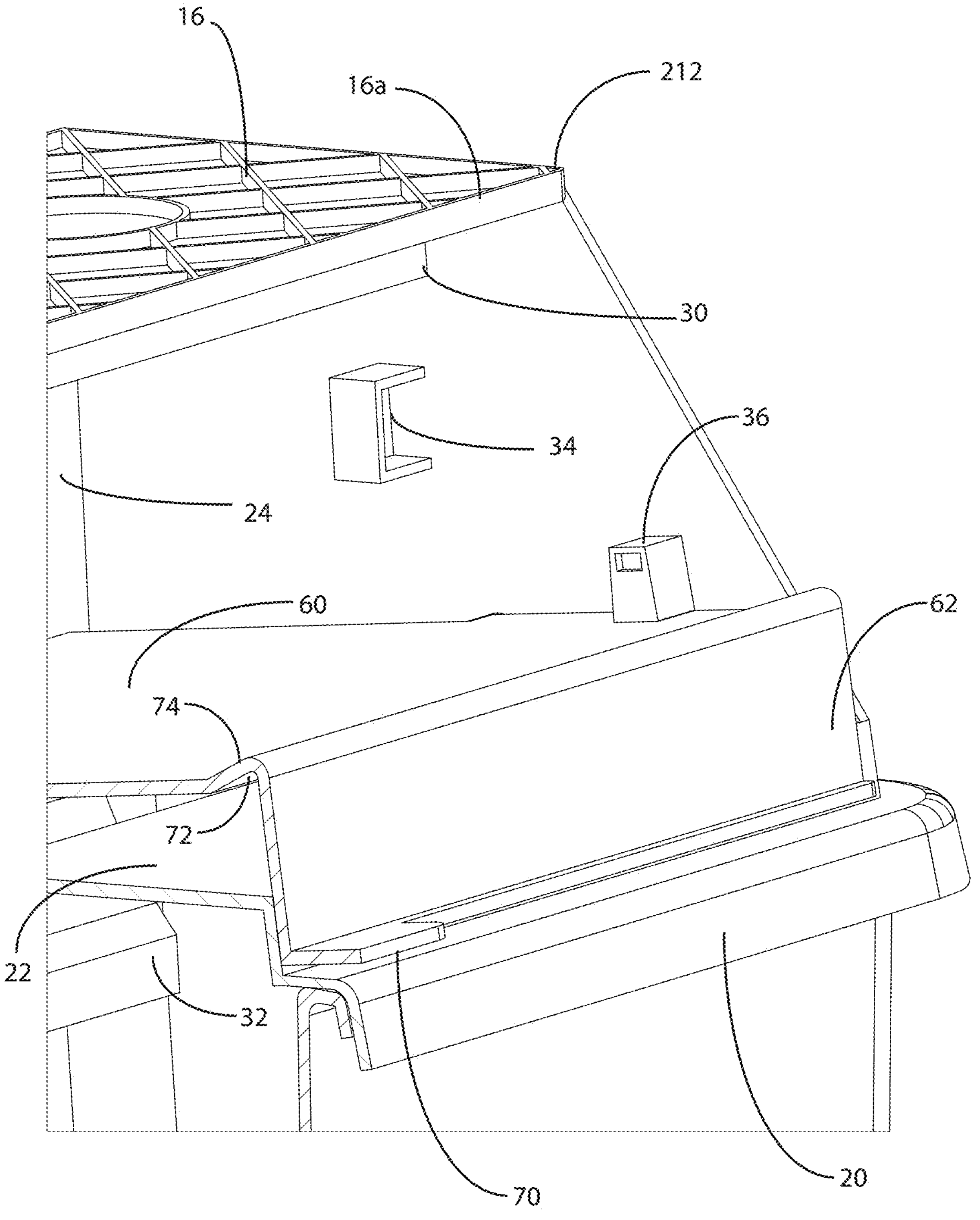
FIG. 7 is a side cut-away view of the interior of the disposable container with the closure flap in a completely open position.

FIGS. 4-7 illustrate the relative positions of the closure flap 12 in the assembled container 6. During use, the closure flap 12 is pivotally movable between a normal closed, unlocked position (not shown), and a fully opened position as shown in FIG. 7. As shown in FIG. 4, the closure flap 12 may be permanently closed and locked for transport and disposal. In the normal closed position, the upper portion 62 of the closure flap does not touch the upper wall 16 of the lid 10; the container is never fully closed and locked until the hooks 36 are inserted into through slots 34 at which point the container 6 is locked for transport and disposal. When in the locked position, the upper portion 62 of the closure flap 12 rests against the front portion **16*a* of the upper wall 16 of the lid 10 and the closure flap detent 72 rests against the interior downward projection 30**.

The closure flap 12 includes a lower portion 60, an upper portion 62, and side portions/walls 64 as well as interior 66 and exterior 68 surfaces. The upper portion 62 of the closure flap 12 includes a central tab 70, which is operable by a user to displace the closure flap 12 between normal closed and open positions. When the tab 70 is pivotally directed downward toward the front shelf 22, the closure flap 12 opens. When released, the closure flap 12 returns to its normal closed position. A detent 72 is provided is provided adjacent to the upper flap portion 62, which when the closure flap 12 is in a permanently locked position rests against the downward projection 30 of an interior upper wall 16 of the lid 10. With respect to the interior surface 66 of the closure flap, the detent 72 provides an inclined surface 74 which works with gravity to direct sharps into the container 6 when the closure flap 12 is moved from an open position to a normal closed position.

The pivotal operation of the closure flap 12 is provided by a plurality of annular axial hubs 42 located at the side edges 64 of the flap in spaced relation with the upper portion 62 of the closure flap 12 such that the mass of lower portion 60 of the closure flap 12 exceeds the mass of the upper portion 62 with the result that the closure flap 12 is gravitationally biased to its normal closed position when released.

Figure 13:
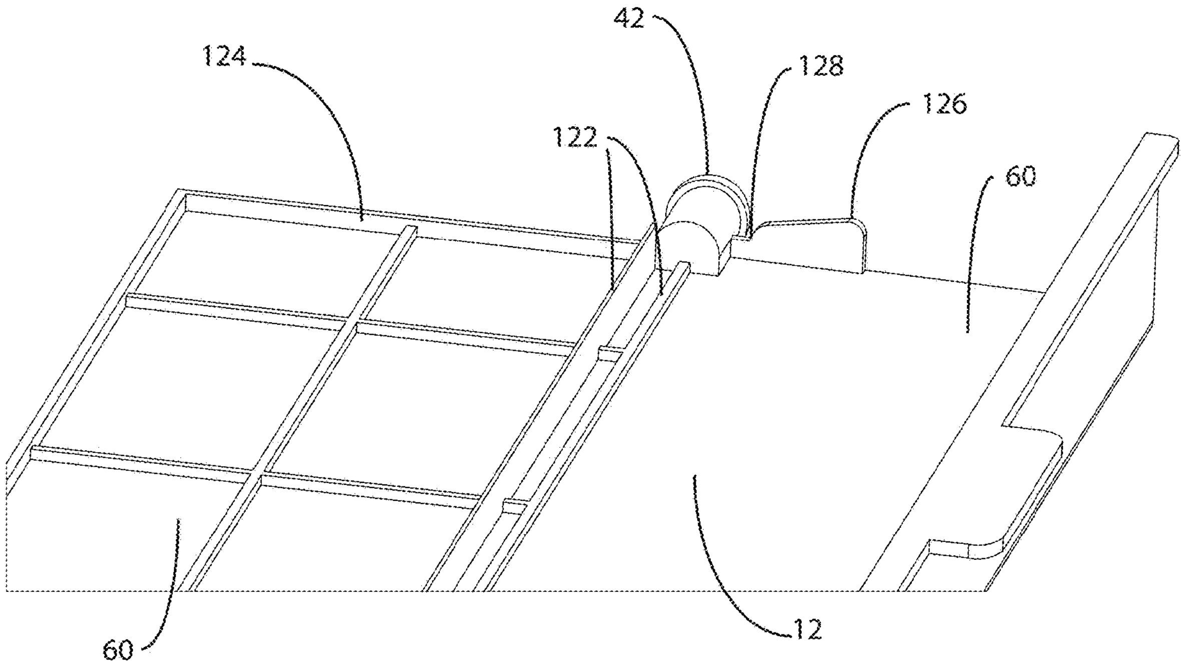
FIG. 13 is partial perspective view of an underside of a closure flap of the container.

As shown in FIG. 13, the closure flap 12 may include various ribs that provide structural rigidity to the closure flap. For example, the flap may include one or more ribs 122 extending across the flap 12 between hubs 42. The flap may also include additional ribs arranged in various appropriate patterns on other portions of the flap. FIG. 13 illustrates, for example, ribs 124 arranged in a generally rectangular pattern across an underside of the lower portion 60 of the flap. In addition, the flap 12 may include a rib 126 that extends from the hub 42 along an edge of the upper portion 62. This rib 126 may include a notch 128 that aids in the installation of the flap 12 into the lid.

Figure 10:
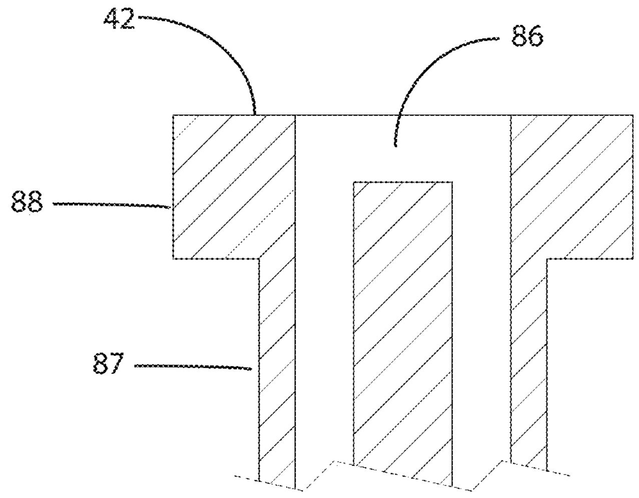
FIG. 10 is a cross-sectional view of the axial hub of the closure flap.

As illustrated in FIGS. 8-10, axial hubs 42 are inserted through openings 38 in the lid 10. The axial hubs 42 include a bearing surface 87 and a flange 88. The flange has a larger diameter than the bearing surface 87. The openings 38 include a circular portion 39 at an upper end of the opening and a generally rectangular lower portion 41. The lower opening portion 41 may extend through the side wall 18 as well as the skirt 26 adjacent the side wall. In this manner, the hub 42 can be inserted through the lower opening 41 and slid upward such that the hub bearing surface 87 engages with the circular opening 39. The circular opening 39 has a diameter that is less that the hub flange 88 so that the flange engages an outside surface of wall 18 adjacent to the semicircular opening 39. The semicircular opening 39 may extend over an arc of 90 degrees, an arc of 180 degrees or an arc of greater than 180 degrees so as to have a snap fit the hub bearing surface 87.

Snap fit covers 14 are provided to maintain the axial hubs 42 in position once inserted through the through openings 38 of the lid 10. The covers 14 include an exterior wall 76, an interior wall 78, side walls 80 and lower wall 82. Locking tabs 44 extending from the side walls 78 in spaced relation with the lower wall 82 and an annular bushing 84 extends from the interior wall 78. After the axial hubs 42 of the closure flap 12 are inserted into the through openings 38 from the interior of the lid 10, the annular bushings 84 of the covers 14 are aligned with the annular opening 86 of the axial hubs 42 and the locking tabs 44 are aligned with the through openings 40 of the lid 10. The diameter of the annular bushing 84 is sized for insertion into the annular opening 86 of the axial hub 42. Once aligned and snapped in place, the cover 14 provides the structural support for the pivotal rotation of the closure flap 12.

What is claimed is:

1. A container for disposal of medical waste comprising:

a receptacle comprising an open top, a bottom wall and a side wall comprising a flange at a top edge of the side wall;

a lid attached to the receptacle, the lid comprising a top wall, a back wall, a side wall, a front wall having an opening sized to permit the introduction of medical waste into the receptacle, a slot, a skirt that attaches to the receptacle side wall flange, and a cowl that extends downwardly into the receptacle below the lid skirt; and a closure flap movable between an open position, a closed position, and a locked position, the closure flap comprising an axial hub extending from a side of the closure flap, a hook, a lower portion, and an upper portion;

wherein the closure flap lower portion and the lid cowl constrict access to an interior of the receptacle when the closure flap is in the open position;

wherein the hook is configured to engage the slot when the closure flap is moved to the locked position; and wherein the slot is positioned in an interior of the lid such that the slot is not accessible when the closure flap is moved to the locked position.

2. The container of claim 1 wherein a mass of the closure flap lower portion is greater than a mass of the closure flap upper portion such that the closure flap is gravitationally biased to the closed position.

3. The container of claim 2 wherein the closure flap axial hub extends from a side of the closure at an intersection of the closure flap upper portion and closure flap lower portion.

4. The container of claim 3 wherein a part of the closure flap lower portion adjacent the intersection of the closure flap upper portion and closure flap lower portion is coplanar with a part of the closure flap upper portion adjacent the intersection of the closure flap upper portion and closure flap lower portion.

5. The container of claim 2 wherein the closure flap lower portion comprises a rib.

6. The container of claim 5 wherein the rib provides structural rigidity to the closure flap lower portion.

7. The container of claim 5 wherein the closure flap upper portion does not comprise a rib.

8. The container of claim 7 wherein the rib provides mass to the closure flap lower portion such that the mass of the closure flap lower portion with the rib is greater than the mass of the closure flap upper portion without the rib.

9. The container of claim 1 wherein the slot is formed on an interior surface of the lid sidewall.

10. The container of claim 9 wherein the hook is configured to enter the slot when the closure flap is moved to the locked position.

11. The container of claim 10 wherein the hook passes through the slot when the closure flap is moved to the locked position.

12. The container of claim 11 wherein once the hook passes through the slot, movement of the closure flap is blocked so that force applied against the closure flap will not move the closure flap from a closed position to an open position.

13. The container of claim 1 wherein the lid cowl comprises an arcuate shape such that a distance between an end of the closure flap lower portion remains consistent as the lid moves from the open to the closed position.

14. The container of claim 1 wherein the closure flap further comprises a second axial hub extending from a second side of the closure flap.

15. The container of claim 14 wherein the closure flap comprises a rib extending between the first and second axial hubs.

16. The container of claim 15 wherein the closure flap comprises a top surface and a bottom surface, and the rib extends from a bottom surface of the closure flap.

17. A container for disposal of medical waste comprising:

a receptacle comprising an open top, a bottom wall and a side wall comprising a flange at a top edge of the side wall;

a lid attached to the receptacle, the lid comprising a top wall, a back wall, a side wall, a front wall having an opening sized to permit the introduction of medical waste into the receptacle, a slot, a skirt that attaches to the receptacle side wall flange, and a cowl that extends downwardly into the receptacle below the lid skirt; and a closure flap movable between an open position, a closed position, and a locked position, the closure flap comprising an axial hub extending from a side of the closure flap, a hook, a lower portion, and an upper portion;

wherein a mass of the closure flap lower portion exceeds a mass of the closure flap upper portion such that the closure flap is gravitationally biased to a closed position;

wherein the hook is configured to engage the slot when the closure flap is moved to the locked position; and wherein the slot is positioned in an interior of the lid such that the slot is not accessible when the closure flap is moved to the locked position.

18. The container of claim 17 wherein the gravitational bias alone is not sufficient to move the closure flap to the locked position.

19. A container for disposal of medical waste comprising:

a receptacle comprising an open top, a bottom wall and a side wall comprising a flange at a top edge of the side wall;

a lid attached to the receptacle, the lid comprising a top wall, a back wall, a side wall, a front wall having an opening sized to permit the introduction of medical waste into the receptacle, a slot, a skirt that attaches to the receptacle side wall flange, and a cowl that extends downwardly into the receptacle below the lid skirt; and a closure flap movable between an open position, a closed position, and a locked position, the closure flap comprising an axial hub extending from a side of the closure flap, a hook, a lower portion, and an upper portion;

wherein the lid skirt comprises locking fingers that engage with the receptacle flange;

wherein the hook is configured to engage the slot when the closure flap is moved to the locked position; and wherein the slot is positioned in an interior of the lid such that the slot is not accessible when the closure flap is moved to the locked position.

20. The container of claim 19 wherein the lid side wall comprises an opening through which the closure flap axial hub extends and a cover that attaches to the lid side wall and covers a portion of the closure flap axial hub that extends through the lid side wall.

* * * * *